United States Patent [19]
Kessel

[11] Patent Number: 5,837,112
[45] Date of Patent: Nov. 17, 1998

[54] ELECTROCHEMICAL MEASURING CELL FOR DETECTING PHOSGENE

[75] Inventor: Robert Kessel, Bad Oldesloe, Germany

[73] Assignee: Drägerwerk AG, Lübeck, Germany

[21] Appl. No.: 895,304

[22] Filed: Jul. 16, 1997

[30] Foreign Application Priority Data

Feb. 28, 1997 [DE] Germany ................. 197 08 038.3

[51] Int. Cl.⁶ .................................................. G01N 27/26
[52] U.S. Cl. ................... 204/415; 204/414; 204/431; 204/432
[58] Field of Search .................... 204/415, 431, 204/432, 414

[56] References Cited

U.S. PATENT DOCUMENTS

| | | | |
|---|---|---|---|
| 3,429,796 | 2/1969 | Lauer | 204/195 |
| 4,049,503 | 9/1977 | Becker et al. | 204/414 |
| 4,202,748 | 5/1980 | Kroneisen | 204/414 |
| 5,518,602 | 5/1996 | Kessel | 204/415 |

FOREIGN PATENT DOCUMENTS 0 531 745 B1  9/1996  European Pat. Off. .

*Primary Examiner*—Bruce F. Bell
*Attorney, Agent, or Firm*—McGlew and Tuttle

[57] ABSTRACT

An electrochemical measuring cell for detecting phosgene, with at least one measuring electrode made of silver and with a counterelectrode in an electrolyte, which contains an organic solvent and to which a conductive salt is added, is improved in terms of the detection of low concentrations of phosgene by adding an amine to the electrolyte.

9 Claims, 1 Drawing Sheet

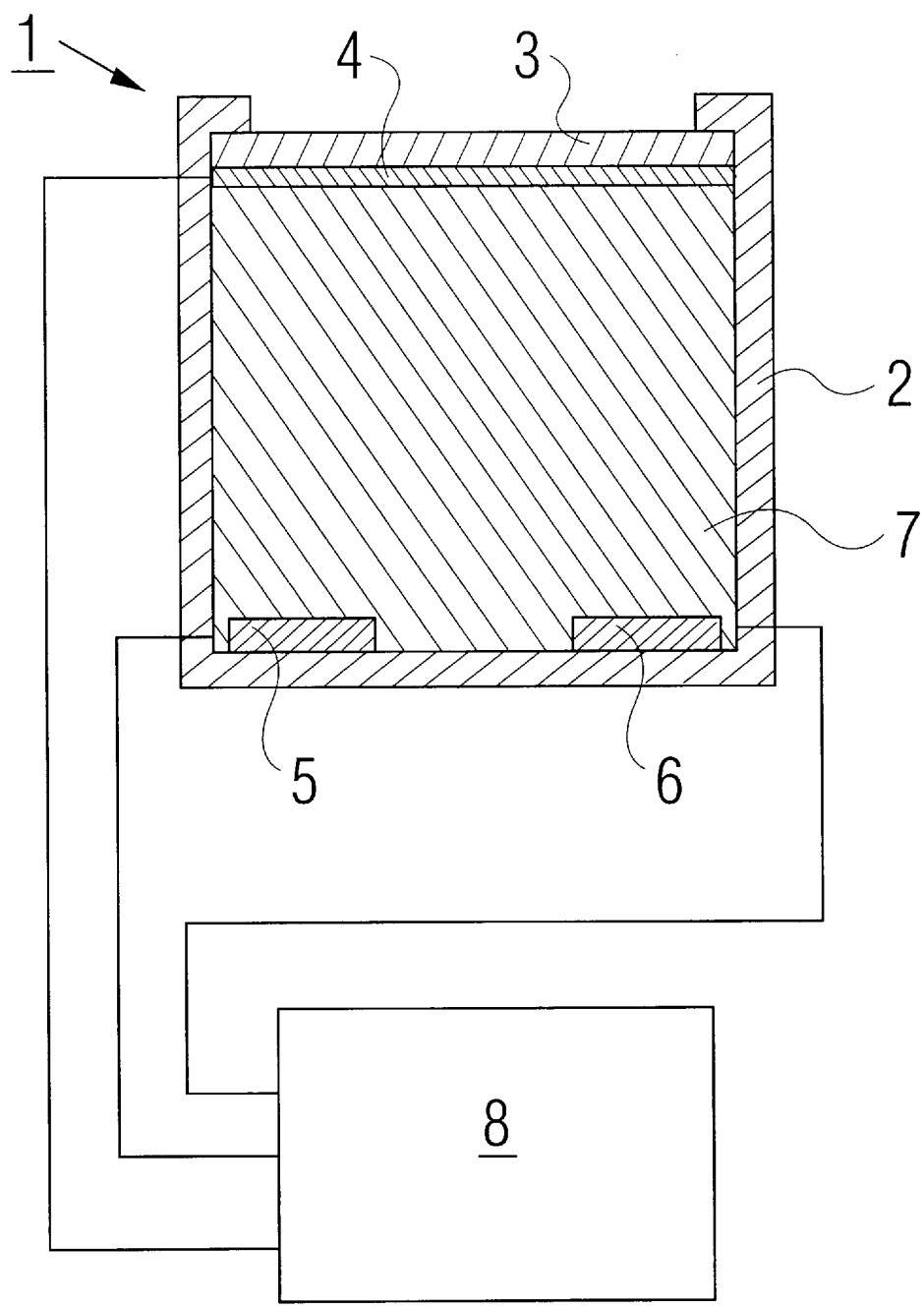

ELECTROCHEMICAL MEASURING CELL FOR DETECTING PHOSGENE

FIELD OF THE INVENTION

The present invention pertains to an electrochemical measuring cell for detecting phosgene, with at least one measuring electrode made of silver and with a counterelectrode in an electrolyte containing an organic solvent, to which electrolyte a conductive salt is added

BACKGROUND OF THE INVENTION

An electrochemical measuring cell of this type has become known from EP 531 745 A2. The prior-art measuring cell comprises a grid-like measuring electrode made of silver behind a diffusion diaphragm, a counterelectrode, which is arranged opposite the measuring electrode and likewise consists of a silver braiding, and an electrolyte connecting the measuring electrode to the counterelectrode. The composition of the electrolyte is based on an organic solvent, to which iron(III) sulfate is added. The prior-art measuring cell delivers a signal level of about 160 nA in the case of exposure to, e.g., 4.8 ppm of phosgene.

The drawback of the prior-art measuring cell is its low sensitivity in the case of the detection of low concentrations of phosgene. For example, the Threshold Limit Values for phosgene are between about 0.02 ppm and 0.1 ppm, which can be resolved with the prior-art measuring cell with difficulty only.

SUMMARY AND OBJECTS OF THE INVENTION

The primary object of the present invention is to improve a measuring cell of this type in terms of the detection of low concentrations of phosgene.

This object is accomplished by adding an amine to the electrolyte.

According to the invention, an electrochemical measuring cell for detecting phosgene is provided with at least one measuring electrode made of silver and with a counterelectrode in an electrolyte containing an organic solvent, to which electrolyte a conductive salt is added, the electrolyte containing an amine as an additional additive.

It was surprisingly found that the sensitivity of detection of the electrochemical measuring cell for phosgene can be markedly increased by adding an organic amine (e.g. aromatic amine) to an electrolyte consisting essentially of an organic solvent. The preferred organic solvents for the electrolyte include propylene carbonate, ethylene carbonate, and γ-butyrolactone, admixtures thereof.

The suitable conductive electrolytes include, e.g., $(NR_4)F$, $(NR_4)BF_4$, $(NR_4)PF_6$, $LiBF_4$, $LiPF_6$, and $LiAsF_6$, R being an alkyl group, especially a lower alkyl group (e.g. of 1–4 carbon atoms) such as methyl.

The suitable amines include, in particular, aromatic amines. The aromatic amines are selected especially advantageously from the group comprising p-dimethylaminobenzaldehyde $[(CH_3)_2N—C_6H_4—CHO]$ N,N' dimethylaniline $[(CH_3)_2N—C_6H_5]$, p-dimethylaminobenzaldehyde in an admixture with dimethylaniline, 3,3',5,5'-tetramethylbenzidine $[(NH_2—)(CH_3—)(CH_3—)—C_6H_2—C_6H_2—(—CH_3)(—CH_3)(—NH_2)]$ tetramethyl-1,4-diphenylenediamine $[(NH_2—)(CH_3—)_4(—C_{12}H_4—)(—NH_2)]$, and N,N,N',N'-tetramethylbenzidine $[(CH_3)_2N—C_6H_4—C_6H_4—N(CH_3)_2]$.

The measuring electrode of the measuring cell according to the present invention consists of a silver diffusion electrode. The preferred material for the counterelectrode and a reference electrode is likewise silver, but precious metals, e.g., gold or platinum, may be used as well. The electrolyte may be in the form of a gel electrolyte or of a liquid electrolyte.

One exemplary embodiment of the present invention is shown in the FIGURE and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic sectional view of an electrochemical measuring cell according to the invention.

DESCRIPTION OF THE PREFERRED EMBODIMENTS

The only FIGURE schematically shows an electrochemical measuring cell 1, with a measuring cell housing 2, whose interior space is closed with a PTFE (i.e. polytetrafluorcethylene, e.g. Teflon) diffusion diaphragm 3 against the atmosphere containing the phosgene to be detected. The interior space of the measuring cell housing 2, which is filled with an electrolyte 7, contains a diffusion measuring electrode 4 behind the diffusion diaphragm 3, as well as a reference electrode 5 and a counterelectrode 6. The electrodes 4, 5, 6 consist of silver and are connected to an evaluating circuit 8, which contains a potentiostat, not shown in the FIGURE. The operating potential can be set between about −200 mV and +200 mV. Especially good results are obtained with a potential in the range of 0 mV, because the basic current is lowest at this potential. The electrolyte consists essentially of a mixture of propylene carbonate and ethylene carbonate with tetramethylammonium tetrafluoroborate as the conductive salt and 3,3',5,5'-tetramethylbenzidine as the aromatic amine. A measuring cell 1 of such a design delivers a signal current of about 1,500 nA in the case of exposure to 1 ppm of phosgene.

Also preferred is the example above repeated with the above except the electrolyte consists essentially of a mixture of propylene carbonate and ethylene carbonate with tetramethylammonium tetrafluoroborate as the conductive salt and p-dimethylaminobenzaldehyde as the aromatic amine. Similar results are obtained.

Also preferred is the example above repeated with the above except the electrolyte consists essentially of a mixture of propylene carbonate and ethylene carbonate with tetramethylammonium tetrafluoroborate as the conductive salt and N,N' dimethylaniline as the aromatic amine. Similar results are obtained.

Also preferred is the example above repeated with the above except the electrolyte consists essentially of a mixture of propylene carbonate and ethylene carbonate with tetramethylammonium tetrafluoroborate as the conductive salt and p-dimethylaminobenzaldehyde in a mixture with dimethylaniline as the aromatic amine. Similar results are obtained.

Also preferred is the example above repeated with the above except the electrolyte consists essentially of a mixture of propylene carbonate and ethylene carbonate with tetramethylammonium tetrafluoroborate as the conductive salt and tetramethyl-1,4-diphenylenediamine as the aromatic amine. Similar results are obtained.

Also preferred is the example above repeated with the above except the electrolyte consists essentially of a mixture of propylene carbonate and ethylene carbonate with tetramethylammonium tetrafluoroborate as the conductive salt and N,N,N',N'-tetramethylbenzidine as the aromatic amine. Similar results are obtained.

The organic amine is desirably an aromatic amine, such as substituted or unsubstituted phenyl amine, biphenyl amine and the like, including optionally formyl (i.e. —CHO) and alkyl, especially lower alkyl (e.g. of 1–4 carbon atoms), groups as ring substituents, and alkyl, especially lower alkyl (e.g. of 1–4 carbon atoms), groups as amino substituents.

In particular, the aromatic amine may have the formula $R'_2N—Ar—(NR'_2)_n$ wherein each R' is hydrogen or alkyl, especially lower alkyl (e.g. of 1–4 carbon atoms), and more particularly wherein R' is hydrogen or methyl; Ar is aryl, especially phenyl or biphenyl (such as p-biphenyl); n is 0 or 1, and particularly 0 or 1 when Ar is phenyl and 1 when Ar is diphenyl; and more particularly wherein Ar is optionally substituted with formyl and/or alkyl groups, such as with formyl and/or with 1–4 alkyl, especially lower alkyl (e.g. of 1–4 carbon atoms), such as methyl.

Particularly preferred aromatic amines contemplated herein are p-dimethylaminobenzaldehyde, N,N' dimethylaniline, mixtures thereof, 3,3',5,5'-tetramethylbenzidine, tetramethyl-1,4-diphenylenediamine, and/or N,N,N',N-tetramethylbenzidine.

While specific embodiments of the invention have been shown and described in detail to illustrate the application of the principles of the invention, it will be understood that the invention may be embodied otherwise without departing from such principles.

What is claimed is:

1. An electrochemical measuring cell for detecting phosgene, comprising:

a measuring electrode made of silver;

a counterelectrode;

an electrolyte containing an organic solvent, said counterelectrode being provided in said electrolyte;

a conductive salt added to said electrolyte; and an amine provided as an additional additive to said electrolyte, wherein said amine is an aromatic amine.

2. The electrochemical measuring cell in accordance with claim 1, wherein said aromatic amine is selected from the group comprising:

p-dimethylaminobenzaldehyde,

N,N' dimethylaniline, p-dimethylaminobenzaldehyde with dimethylaniline, 3,3',5,5'-tetramethylbenzidine, tetramethyl-1,4-diphenylenediamine, and N,N,N',N'-tetramethylbenzidine.

3. The electrochemical measuring cell in accordance with claim 2, wherein said electrolyte contains a mixture of propylene carbonate and ethylene carbonate as the organic solvent.

4. The electrochemical measuring cell in accordance with claim 1, wherein said electrolyte contains a mixture of propylene carbonate and ethylene carbonate as the organic solvent.

5. The electrochemical measuring cell in accordance with claim 1, wherein said electrolyte contains a mixture of propylene carbonate and ethylene carbonate as the organic solvent.

6. A method of electrochemically detecting phosgene, the method comprising:

exposing an atmosphere containing phosgene to be detected to an electrochemical measuring cell which is capable of generating a signal current indicative of the presence of phosgene, which cell has been formed by the steps of;

providing a measuring electrode made of silver, a counterelectrode and an electrolyte containing an organic solvent, said counterelectrode being provided in said electrolyte;

adding a conductive salt to said electrolyte; and adding an amine to said electrolyte as an additional additive wherein said amine is an aromatic amine; and measuring the resulting generated signal current for detecting the presence of phosgene.

7. The method in accordance with claim 6, wherein said aromatic amine is selected from the group comprising:

p-dimethylaminobenzaldehyde,

N,N' dimethylaniline, p-dimethylaminobenzaldehyde with dimethylaniline, 3,3',5,5'-tetramethylbenzidine, tetramethyl-1,4-diphenylenediamine, and N,N,N',N'-tetramethylbenzidine.

8. The method in accordance with claim 6, wherein said electrolyte contains a mixture of propylene carbonate and ethylene carbonate as the organic solvent.

9. The method in accordance with claim 6, wherein said measuring cell is effective for generating a signal current of about 1,500 nA upon exposure to 1 ppm of phosgene.

* * * * *